(12) United States Patent
Mehta et al.

(10) Patent No.: US 9,504,727 B2
(45) Date of Patent: *Nov. 29, 2016

(54) ORAL DELIVERY OF PEPTIDE PHARMACEUTICAL COMPOSITIONS

(71) Applicant: UGP Therapeutics, Inc., Chicago, IL (US)

(72) Inventors: Nozer M. Mehta, Randolph, NJ (US); William Stern, Tenafly, NJ (US); James P. Gilligan, Union, NJ (US)

(73) Assignee: Enteris BioPharma, Inc., Boonton, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 14/484,745

(22) Filed: Sep. 12, 2014

(65) Prior Publication Data

US 2015/0125522 A1 May 7, 2015

Related U.S. Application Data

(63) Continuation of application No. 13/219,132, filed on Aug. 26, 2011, now Pat. No. 8,835,377, which is a continuation of application No. 11/144,580, filed on Jun. 2, 2005, now abandoned.

(60) Provisional application No. 60/580,872, filed on Jun. 18, 2004.

(51) Int. Cl.
| | |
|---|---|
| *A61K 38/08* | (2006.01) |
| *A61K 9/00* | (2006.01) |
| *A61K 9/48* | (2006.01) |
| *A61K 38/06* | (2006.01) |
| *A61K 38/07* | (2006.01) |
| *A61K 47/18* | (2006.01) |
| *A61K 47/26* | (2006.01) |

(52) U.S. Cl.
CPC ............. *A61K 38/08* (2013.01); *A61K 9/0053* (2013.01); *A61K 9/0095* (2013.01); *A61K 9/4858* (2013.01); *A61K 9/4891* (2013.01); *A61K 38/06* (2013.01); *A61K 38/07* (2013.01); *A61K 47/183* (2013.01); *A61K 47/26* (2013.01)

(58) Field of Classification Search
CPC .......................... A61K 38/08; A61K 9/0053
USPC ........................................ 514/1.1, 21.6, 21.7
See application file for complete search history.

(56) References Cited

U.S. PATENT DOCUMENTS

| | | | |
|---|---|---|---|
| 4,339,428 A * | 7/1982 | Tencza ................. | A61K 9/4808 424/451 |
| 4,507,276 A * | 3/1985 | Tencza ................. | A61K 9/5084 424/459 |
| 4,693,896 A * | 9/1987 | Wheatley ............... | A61K 31/60 424/480 |
| 4,857,335 A | 8/1989 | Bohm | |
| 4,963,525 A | 10/1990 | Alexander et al. | |
| 5,122,376 A * | 6/1992 | Aliverti ................ | A61K 9/0043 424/405 |
| 5,126,327 A | 6/1992 | Takeuchi et al. | |
| 5,272,175 A | 12/1993 | Hansen et al. | |
| 5,312,899 A | 5/1994 | Schiller | |
| 5,534,496 A * | 7/1996 | Lee ..................... | A61K 38/1709 424/434 |
| 5,602,100 A | 2/1997 | Brown et al. | |
| 5,709,879 A | 1/1998 | Barchfeld et al. | |
| 5,853,705 A | 12/1998 | Nakayama et al. | |
| 5,912,014 A * | 6/1999 | Stern ................... | A61K 9/4858 424/426 |
| 5,952,004 A | 9/1999 | Rudnic et al. | |
| 6,086,918 A | 7/2000 | Stern et al. | |
| 6,184,226 B1 * | 2/2001 | Chakravarty ........ | A61K 31/519 514/266.21 |
| 6,423,334 B1 * | 7/2002 | Brayden ................ | A61K 47/14 424/400 |
| 6,468,959 B1 | 10/2002 | Wunderlich et al. | |
| 6,703,483 B1 | 3/2004 | Schiller et al. | |
| 6,878,805 B2 | 4/2005 | Manoharan et al. | |
| 6,946,150 B2 | 9/2005 | Whittle | |
| 7,666,446 B2 | 2/2010 | Choi et al. | |
| 8,377,863 B2 | 2/2013 | Stern et al. | |
| 8,513,183 B2 | 8/2013 | Stern et al. | |
| 8,592,366 B2 | 11/2013 | Stern et al. | |
| 8,664,178 B2 | 3/2014 | Stern et al. | |
| 8,835,377 B2 | 9/2014 | Mehta et al. | |
| 9,399,017 B2 | 7/2016 | Stern et al. | |
| 2003/0032774 A1 | 2/2003 | Brown et al. | |
| 2004/0029796 A1 | 2/2004 | Szeto et al. | |
| 2005/0282756 A1 | 12/2005 | Mehta et al. | |
| 2007/0134279 A1 | 6/2007 | Stern | |
| 2011/0045029 A1 | 2/2011 | Choi et al. | |

(Continued)

FOREIGN PATENT DOCUMENTS

| | | |
|---|---|---|
| EP | 0 350 221 A2 | 1/1990 |
| WO | 95/34295 A1 | 12/1995 |

(Continued)

OTHER PUBLICATIONS

Bastin (Organic Process Research & Development 2000, 4, 427-435, 2000).*

(Continued)

*Primary Examiner* — David Lukton
(74) *Attorney, Agent, or Firm* — Greenberg Traurig, LLP; David J. Dykeman; Natalie Salem

(57) ABSTRACT

Bioavailability of peptide active agents to be administered orally is enhanced by a pharmaceutical composition providing targeted release of the peptide to the intestine by combining the composition with an absorption enhancer. Bioavailability is further significantly increased by administering the composition in an acid-resistant protective vehicle which transports components of the invention through the stomach. The composition may optionally further include a sufficient amount of a pH-lowering agent to lower local intestinal pH. All components are released together into the intestine with the peptide.

25 Claims, 2 Drawing Sheets

(56) References Cited

U.S. PATENT DOCUMENTS

| | | |
|---|---|---|
| 2013/0171248 A1 | 7/2013 | Choi et al. |
| 2014/0255479 A1 | 9/2014 | Carl et al. |

FOREIGN PATENT DOCUMENTS

| | | |
|---|---|---|
| WO | 97/33531 A1 | 9/1997 |
| WO | 99/64449 A2 | 12/1999 |
| WO | 00/55189 A1 | 9/2000 |
| WO | 01/27154 A2 | 4/2001 |
| WO | 01/54514 A1 | 8/2001 |
| WO | 02/05748 A2 | 1/2002 |
| WO | 02/22152 A2 | 3/2002 |
| WO | 02/072075 A1 | 9/2002 |
| WO | 2008/150426 | 12/2008 |
| WO | 2012/174117 | 12/2012 |

OTHER PUBLICATIONS

European communication dated Sep. 9, 2010 issued in connection with European Patent Application No. 05 757 462.6.
Canadian Intellectual Property Office, Office Action dated Oct. 22, 2010 issued in connection with Canadian Patent Application No. 2,570,311.
Nicolaus, "Symbiotic Approach to Drug Design," Decision Making in Drug Research, (Jan. 1, 1983), pp. 173-186.
Supplementary European Search Report dated Apr. 14, 2010 issued in connection with European Patent Application No. 05 757 462.6.
LeCluyse, et al., "Relationship Between Drug Absorption Enhancing Activity and Membrane Perturbing Effects of Acylcarnitines," Pharmaceutical Research, vol. 8, No. 1, 1991, pp. 84-87.
Canadian Office Action dated Nov. 3, 2009 relating to Canadian Patent Application No. 2,570,311.
Sinko et al., "Biopharmaceutical approaches for developing and assessing oral peptide delivery strategies and systems: In Vitro permeability and In Vivo oral absorption of salmon calcitonin (sCT)", Pharmaceutical Research, vol. 16, No. 4, pp. 527-533, 1999.
Ogawa et al., "Synthesis and antinociceptive activity of orally active opioid peptides: Improvement of oral biavailability by esterification", Chemical Pharmaceutical Bulletin, vol. 51, No. 7, pp. 759-771, 2003.
Wan et al., "Quantification of [Dmt1]DALDA in ovine plasma by on-line liquid chromatography/quadrupole time-of-flight mass spectrometry", Rapid Commun Mass Spectrom., 17(6):538-46, 2003, abstract, <<http://www.ncbi.nlm.nih.gov/pubmed/12621615?dopt-Abstract>>.
Wu et al., "A highly potent peptide analgesic that protects against ischemia-reperfusion-induced myocardial stunning", Am J. Physiol Heart Circ. Physiol, Aug. 2002, 283(2):H783-H791.
European Search Report dated Aug. 30, 2005 issued in connection with European Patent Appln. No. 01996021.0.
International Search Report dated Oct. 26, 2005 issued in connection with International Application No. PCT/US05/20255.
Takahashi et al.; "Production of Bioactive Salmon Calcitonin From the Nonendocrine Cell Lines COS-7 and CHO", Peptides, vol. 18, No. 3, pp. 439-444, 1997.
Lu et al.; "TAP-Independent Presentation 1 of CTL Epitopes by Trojan Antigens", Journal of Immunology, vol. 166, No. 12, pp. 7063-7071, Jun. 15, 2001.
Official Action issued in connection with U.S. Appl. No. 11/144,580 dated Mar. 7, 2011.
Official Action issued in connection with U.S. Appl. No. 11/144,580 dated Dec. 15, 2009.
Official Action issued in connection with U.S. Appl. No. 11/144,580 dated Mar. 6, 2009.
Official Action issued in connection with U.S. Appl. No. 11/144,580 dated Apr. 24, 2008.
Official Action issued in connection with U.S. Appl. No. 11/144,580 dated Jul. 20, 2007.
Official Action issued in connection with U.S. Appl. No. 11/144,580 dated Jul. 17, 2006.
Official Action issued in connection with U.S. Appl. No. 13/219,132 dated Mar. 7, 2014.
Official Action issued in connection with U.S. Appl. No. 13/219,132 dated May 20, 2014.
Constantinides et al., "Considerations nad recommendations on traditional and non-traditional uses of excipients in oral drug products", AAPS Open 2:3 (2016).

* cited by examiner

ORAL DELIVERY OF PEPTIDE PHARMACEUTICAL COMPOSITIONS

CROSS REFERENCE TO A RELATED APPLICATION

The present application is a 35 U.S.C. §119 conversion of Provisional Application Ser. No. 60/580,872 filed Jun. 18, 2004

BACKGROUND OF THE INVENTION

1. Field of the Invention

The present invention relates to oral peptide pharmaceutical compositions having analgesic and/or cardiovascular activity, and to methods of enhancing bioavailability of such peptides when administered orally.

2. Description of the Related Art

Opiates such as morphine and codeine, or opiate-like synthetic drugs are currently used for the management of moderate to severe pain. Many endogenous peptides of mammalian and amphibian origin (e.g., the endorphins) also bind to opioid receptors and elicit an analgesic response similar to classic narcotic opiates. This led to the hope that these peptides might be produced commercially and administered to patients to, e.g., relieve pain. It was found, however, that side effects such as depression of cardiac and respiratory function, tolerance, physical dependence capacity and precipitated withdrawal syndrome are caused by nonspecific interactions between such peptides and central nervous system receptors. Such side effects are due to the interaction of these peptides with multiple opioid receptors. For this reason, peptides with a variety of structural modifications have been developed in an effort to develop peptide-based pharmaceuticals that are specific for a particular opioid receptor sub-type [mu, delta and kappa], and which produce long-lasting antinociceptive effects while minimizing undesirable side effects such as depression of cardiac and/or respiratory function, extended sedative activity, etc.

Peptide pharmaceuticals known in the prior art, including the analgesic peptides described above, frequently have been administered by injection or by nasal administration. A more preferred oral administration tends to be problematic because peptide-active compounds are very susceptible to degradation in the stomach and intestines and show poor bioavailability. For example, the prior art is not believed to have reported to achieve reproducible blood levels of opioid peptides when administered orally. This is believed to be because peptides lack sufficient stability in the gastrointestinal tract, and tend to be poorly transported through intestinal walls into the blood. However, injection and nasal administration are significantly less convenient, and involve more patient discomfort, than oral administration. Often this inconvenience or discomfort results in substantial patient noncompliance with a treatment regimen. Thus there is a need in the art for a more effective and reproducible oral administration of peptide pharmaceuticals including, but not limited to, peptide pharmaceuticals having analgesic and/or cardiovascular activity.

Proteolytic enzymes of both the stomach and intestines may degrade peptides, rendering them inactive before they can be absorbed into the bloodstream. Any amount of peptide that survives proteolytic degradation by proteases of the stomach (typically having acidic pH optima) is later confronted with proteases of the small intestine and enzymes secreted by the pancreas (typically having neutral to basic pH optima). Specific difficulties arising from the oral administration of a peptide involve the relatively large size of the molecule, and the charge distribution it carries. This may make it more difficult for such peptides to penetrate the mucus along intestinal walls or to cross the intestinal brush border membrane into the blood. These additional problems may further contribute to limited bioavailability.

SUMMARY OF THE INVENTION

Recent advances in the field of analgesic peptides have been directed towards the derivatization of these peptides to protect against enzymatic or hydrolytic degradation in order to increase their half lives in circulation, and make them more selective for a specific opioid receptor subclass to avoid deleterious and potentially life-threatening side effects. However, even with such stable and protease-resistant analogs, oral delivery is not feasible due to low bioavailability.

It is accordingly an object of the present invention to provide a therapeutically effective oral pharmaceutical composition for reliably delivering pharmaceutical peptides, e.g., physiologically active peptide agents having analgesic and/or cardiovascular activity.

It is a further object of the invention to provide therapeutic methods for enhancing the bioavailability of such peptides.

In one aspect, the invention provides a pharmaceutical composition for the oral delivery of a peptide having analgesic and/or cardiovascular activity. The composition comprises (A) a therapeutically effective amount of an active peptide component (as described below) and (B) at least one absorption enhancer effective to promote bioavailability of the peptide or (C) at least one pharmaceutically acceptable pH-lowering agent, wherein the pH-lowering agent is present in the pharmaceutical composition in a quantity which, if the composition were added to 10 milliliters of 0.1M aqueous sodium bicarbonate solution, would be sufficient to lower the pH of the solution to no higher than 5.5. In a further embodiment (D), the pharmaceutical composition may include both the absorption enhancer and the pH-lowering agent. In yet a further embodiment (E), the pharmaceutical composition of (A), (B), (C) or (D) may also include an acid-resistant protective vehicle effective to transport the pharmaceutical composition through the stomach of a patient while preventing contact between the active peptide component and stomach proteases.

In another aspect, the invention is directed to a pharmaceutical composition for the oral delivery of a peptide having analgesic and/or cardiovascular activity, wherein the composition comprises (A) a therapeutically effective amount of an active peptide component (as described below) and (B) at least one pharmaceutically acceptable pH-lowering agent, wherein the pH-lowering agent is present in the pharmaceutical composition in a quantity which, if the composition were added to 10 milliliters of 0.1M aqueous sodium bicarbonate solution, would be sufficient to lower the pH of the solution to no higher than 5.5. The pharmaceutical composition may optionally additionally comprise at least one additional component selected from the group consisting of (C) at least one absorption enhancer effective to promote bioavailability of the peptide; and (D) an acid-resistant protective vehicle effective to transport the pharmaceutical composition through the stomach of a patient while preventing contact between the active peptide component and stomach proteases.

The active peptide component for inclusion in the formulation of the invention is selected from among one or more of the following:

(A) A peptide of formula I $$H_2N-\underset{R^2}{\overset{R^1}{C}}-X-\left[Y-\underset{R^2}{\overset{R^1}{C}}-X\right]_n-Y-\underset{R^2}{\overset{R^1}{C}}-\underset{O}{\overset{\|}{C}}-NH_2$$

wherein $R^1$ is selected from the group consisting of hydrogen, $C_1$-$C_7$ branched or unbranched alkyl, phenyl, hydroxyphenyl, methoxyphenyl, benzyl, hydroxybenzyl, methoxybenzyl, aminobenzyl, amidobenzyl, carboxybenzyl, carboxymethylbenzyl, cyanobenzyl, fluorobenzyl, chlorobenzyl, bromobenzyl, iodobenzyl, mercaptobenzyl, and nitrobenzyl;

$R^2$ is hydrogen, methyl, ethyl; or $R^1$ and $R^2$, taken together with the carbon atom to which they are attached, form a cycloalkyl ring containing 3-5 carbon atoms;

X is selected from the group consisting of C=O, N—H, $CH_2$, —O—, C=S and —S—;

Y is selected from the group C=O, N—H, $CH_2$, —O—, C=S and —S—; or

X and Y, taken together, represent an olefin linkage wherein X and Y each have a hydrogen atom attached thereto in a cis or trans configuration; and n is 1-7;

(B) a peptide of formula II:

H-Tyrosine-A-Phenylalanine-B—NH2 wherein:

A is selected from the group consisting of D-α-amino acids;

B is selected from the group consisting of α-amino acids; and the overall net positive charge of the peptide is +2 or greater, (C) A peptide of formula III

[Structure of formula III showing peptide with OH, HN=C(NH)NH, $R^1$-$R^9$ substituents, CH, CH$_2$, (CH$_2$)$_3$, and C=O linkages with NH$_2$ terminus, including D]

wherein $R^1$ is selected from
(i) linear or branched $C_1$-$C_6$ alkyl;
(ii) $C_1$-$C_6$ alkoxy;

$R^2$ is selected from
(i) hydrogen;
(ii) linear or branched $C_1$-$C_6$ alkyl;
(iii) $C_1$-$C_6$ alkoxy;

$R^3$ and $R^4$ is each and independently selected from
(i) hydrogen;
(ii) linear or branched $C_1$-$C_6$ alkyl;

(iii) —(CH$_2$)$_m$—phenyl wherein m=1-3;

(iv) —CH$_2$—cyclopropyl; and (v) —CH$_2$—CH=CH$_2$;

$R^5$, $R^6$, $R^7$, $R^8$ and R9 is each independently selected from
(i) hydrogen;
(ii) halogen, where "halogen" encompasses chloro, fluoro, bromo and iodo; and
(iii) linear or branched $C_1$-$C_6$ alkyl; and n is an integer of from 1 to 5;

(D) A peptide of formula IV

Tyrosine-D-alanine-Xaa-Glycine-Tyrosine-Proline-Serine-NH$_2$ wherein Xaa is L- or D-dimethylphenylalanine;

(E) A peptide of formula V

Tyrosine-D-alanine-Xaa-Glutamic Acid-Valine-Valine-Glycine-NH$_2$ wherein Xaa is L- or D-dimethylphenylalanine;

(F) An enkephalin peptide; and (G) A peptide linked to a DMT-Tic-pharmacophore.

In another aspect, the invention provides a pharmaceutical composition for oral delivery of a compound having analgesic and/or cardiovascular activity, wherein the composition comprises: (A) a therapeutically effective amount of an active compound which is an agonist or a partial agonist of vanilloid receptor VR1; and (B) at least one absorption enhancer effective to promote bioavailability of the compound or (C) at least one pharmaceutically acceptable pH-lowering agent, wherein the pH-lowering agent is present in the pharmaceutical composition in a quantity which, if the composition were added to 10 milliliters of 0.1M aqueous sodium bicarbonate, would be sufficient to lower the pH of the solution to no higher than 5.5. In a further embodiment (D), the pharmaceutical composition may include both the absorption enhancer and the pH-lowering agent. In yet another embodiment (E), the pharmaceutical composition of (A), (B), (C) or (D) may also include an acid-resistant protective vehicle effective to transport the pharmaceutical composition through the stomach of a patient while preventing contact between the active peptide component and stomach proteases.

In a further aspect, any of the pharmaceutical compositions of the invention may additionally comprise a water-soluble barrier separating the pH-lowering agent from the protective vehicle.

In another aspect of the invention, any of the pharmaceutical compositions may comprise granules containing a pharmaceutical binder and, uniformly dispersed in the binder, at least one of the pH-lowering agent, the absorption enhancer and the peptide having analgesic and/or cardiovascular activity.

Additional aspects of the invention relate to therapeutic methods involving oral administration of therapeutically effective amounts of pharmaceutical compositions as described herein.

In one aspect, the invention provides a method for enhancing the oral bioavailability of a compound comprising a peptide having analgesic or cardiovascular activity. The method comprises orally delivering a pharmaceutical composition that combines the compound with at least one absorption enhancer effective to promote bioavailability of the compound, or combining the compound with at least one pH-lowering agent, wherein the pH-lowering agent is present in a quantity which, if the composition were added to 10 milliliters of 0.1 M aqueous sodium bicarbonate solution, would be sufficient to lower the pH of the solution to no higher than 5.5. The method may also comprise orally delivering a pharmaceutical composition that combines the compound with at least one absorption enhancer in combination with at least one pH-lowering agent. The method may also comprise transporting any of the above pharmaceutical compositions through the stomach of a patient by an acid-resistant protective vehicle to prevent contact between the pharmaceutical composition and stomach proteases.

In another aspect, the invention provides a method for stimulating a mu, delta or kappa-opioid receptor in a mammal in need of such stimulation, wherein the method comprises orally administering to the mammal an effective opioid receptor stimulating amount of one or more of the pharmaceutical compositions described herein.

In an additional aspect, the invention provides a method for relieving pain comprising orally administering to a patient in need of pain relief an effective pain-relieving amount of one or more of the pharmaceutical compositions described herein.

In a further aspect, the invention provides a method for improving myocardial contractile force. The method comprises orally administering to a patient in need of such improvement an effective contractile force-increasing amount of one or more of the pharmaceutical compositions described herein containing a therapeutically effective amount of a dermorphin analog or a prodrug thereof.

In another aspect, the invention provides a method for improving cardiac performance of a heart before, during and/or after cardiac transplantation. The method comprises orally administering to a patient in need of such improved cardiac performance an effective cardiac performance-improving amount of one or more of the pharmaceutical compositions described herein containing a therapeutically effective amount of a dermorphin analog or a prodrug thereof.

In the context of the invention, prodrugs of any of the above-described active peptides useful in forming the compositions of the invention may be used in place of the corresponding peptide, as these will also increase the serum levels of the peptide. The prodrug is converted in vivo to the desired active compound by a well-known mechanism. The pharmaceutical industry frequently uses salt or ester prodrugs to deliver a large number of pharmaceutical agents. It is, in fact, rare in the pharmaceutical industry that particular active ingredients that are to be delivered to the bloodstream of a patient are not formulated (in their dosage form) as a prodrug which, as noted above, is subsequently converted in vivo to the desired active compound by such well-known mechanism. The term "prodrug" as used herein is meant to include only those compounds which, when converted in vivo, deliver one or more of the active peptides described and claimed herein to the bloodstream of a subject to whom they are administered. A variety of well-known prodrug forms of various functional groups that may appear on the active peptide compounds for use in the invention are set forth in *A Textbook of Drug Design and Development*, Bundgaard and Krosgaard-Larsen, Ed., (Harwook Academic Publishers GmfH, Chur, Switzerland) 1991 which is incorporated herein by reference.

Other features and advantages of the present invention will become apparent from the following detailed description of the invention.

DETAILED DESCRIPTION OF THE INVENTION

Figure 1:
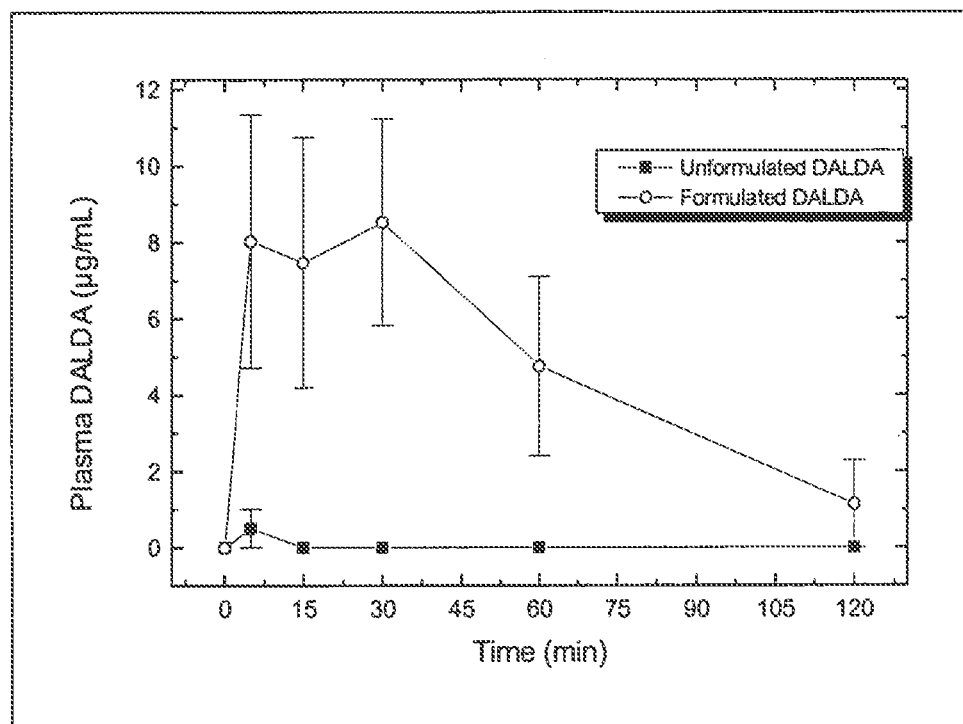
FIG. 1 provides, in graphical form, pharmacokinetic profiles following administration of unformulated Dmt-DALDA and Dmt-DALDA formulated with an absorption enhancer and pH-lowering agent by duodenal injection in anesthetized rats.

In accordance with the invention, patients in need of treatment with peptides having analgesic and/or cardiovascular activity are provided with an oral pharmaceutical composition thereof (at appropriate dosage), preferably but not necessarily in tablet or capsule form of an ordinary size in the pharmaceutical industry. The dosages and frequency of administering the products are discussed in more detail below. Patients who may benefit are any who suffer from disorders that respond favorably to increased levels of a peptide-containing compound. For example, oral administration of dermorphin, deltorphin and/or enkephalin peptide analogs in accordance with the invention may be used to treat patients in need of pain relief, or those with conditions warranting improved cardiac performance, e.g., by improving myocardial contractile force.

Without intending to be bound by theory, the pharmaceutical compositions of the invention are believed to overcome a series of different and unrelated natural barriers to bioavailability. Various components of the pharmaceutical compositions act to overcome different barriers by mechanisms appropriate to each, and result in synergistic effects on the bioavailability of a peptide active ingredient.

The peptide active compound may be administered orally. In accordance with the invention, proteolytic degradation of the peptide by stomach proteases (most of which are active in the acid pH range) and intestinal or pancreatic proteases (most of which are active in the neutral to basic pH range) is reduced. Solubility enhancers aid passage of the peptide active agent through the intestinal epithelial barrier.

Again, without intending to be bound by theory, it appears that, in accordance with one embodiment of the present invention, the peptide is transported through the stomach under the protection of an appropriate acid-resistant protective vehicle for substantially preventing contact between the active peptide and any stomach proteases capable of degrading it. Once the pharmaceutical composition of the invention passes through the stomach and enters the intestinal region where basic to neutral pH predominates, and where proteases tend to have basic to neutral pH optima, the enteric coating or other vehicle releases the peptide and acid (in close proximity to each other).

The pH-lowering agent is believed to lower the local intestinal pH (where the active agent has been released) to levels below the optimal range for many intestinal proteases. This decrease in pH reduces the proteolytic activity of the intestinal proteases, thus affording protection to the peptide from potential degradation. The activity of these proteases is diminished by the temporarily acidic local environment provided by the invention. It is preferred that sufficient acid be provided that local intestinal pH is lowered temporarily to 5.5 or below, preferably 4.7 or below and more preferably 3.5 or below. The sodium bicarbonate test described below (in the section below captioned "the pH-Lowering Agent") is indicative of the required acid amount. Preferably, conditions of reduced intestinal pH persist for a time period sufficient to protect the peptide agent from proteolytic degradation until at least some of the peptide agent has had an opportunity to cross the intestinal wall into the bloodstream. The absorption enhancers of the invention synergistically promote peptide absorption into the blood while conditions of reduced proteolytic activity prevail.

The mechanism by which the invention is believed to accomplish the goal of enhanced bioavailability is aided by having active components of the pharmaceutical composition released together as simultaneously as possible. To this end, it is preferred to keep the volume of enteric coating as low as possible consistent with providing protection from stomach proteases. Thus enteric coating is less likely to interfere with peptide release, or with the release of other components in close time proximity with the peptide. The enteric coating should normally add less than 30% to the weight of the remainder of pharmaceutical composition (i.e., the other components of the composition excluding enteric coating). Preferably, it is less than 20% and, more preferably, the enteric coating adds between 10% and 20% to the weight of the uncoated ingredients.

The absorption enhancer which may be a solubility enhancer and/or transport enhancer (as described in more detail below) aids transport of the peptide agent from the intestine to the blood, and may promote the process so that it better occurs during the time period of reduced intestinal pH and reduced intestinal proteolytic activity. Many surface active agents may act as both solubility enhancers and transport (uptake) enhancers. Again without intending to be bound by theory, it is believed that enhancing solubility provides (1) a more simultaneous release of the active components of the invention into the aqueous portion of the intestine, (2) better solubility of the peptide in, and transport through, a mucous layer along the intestinal walls. Once the peptide active ingredient reaches the intestinal walls, an uptake enhancer provides better transport through the brush border membrane of the intestine into the blood, via either transcellular or paracellular transport. As discussed in more detail below, many preferred compounds may provide both functions. In those instances, preferred embodiments utilizing both of these functions may do so by adding only one additional compound to the pharmaceutical composition. In other embodiments, separate absorption enhancers may provide the two functions separately.

Each of the preferred ingredients of the pharmaceutical composition of the invention is separately discussed below. Combinations of multiple pH-lowering agents, or multiple enhancers can be used as well as using just a single pH-lowering agent and/or single enhancer. Some preferred combinations are also discussed below.

In one embodiment of the present invention, the pharmaceutical composition for oral delivery may comprise the peptide or compound in combination with an absorption enhancer and a pH-lowering agent, along with an enteric coating to transport the ingredients through the stomach of a patient while preventing contact between the pharmaceutical composition and stomach proteases.

In another embodiment, it has been shown from experiments with several peptides that a pharmaceutical composition for oral delivery that comprises only a peptide with a pH-lowering agent provides a significant increase in bioavailability compared to that offered by the peptide taken alone.

In yet another embodiment, it has been shown from experimentation with a variety of peptides that a pharmaceutical composition for oral delivery comprising only a peptide and an absorption enhancer provides a significant increase in bioavailability, compared to that of the peptide taken alone.

Peptide Active Ingredients

Peptide active ingredients which may benefit from oral delivery in accordance with the invention include peptides having analgesic or cardiovascular activity. Several non-limiting examples of such peptides are described below, however, as one of ordinary skill in this art would recognize, various additional peptides, analogs and/or prodrugs may be substituted for the peptides described herein in the formulations prepared according to the invention.

In a first embodiment, a peptide for use with the invention may be a dermorphin analog, or a prodrug thereof, of formula I

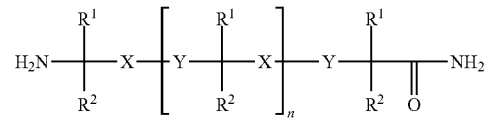

wherein $R^1$ is selected from the group consisting of hydrogen, $C_1$-$C_7$ branched or unbranched alkyl, phenyl, hydroxyphenyl, methoxyphenyl, benzyl, hydroxybenzyl, methoxybenzyl, aminobenzyl, amidobenzyl, carboxybenzyl, carboxymethylbenzyl, cyanobenzyl, fluorobenzyl, chlorobenzyl, bromobenzyl, iodobenzyl, mercaptobenzyl, and nitrobenzyl;

$R^2$ is hydrogen, methyl, ethyl; or $R^1$ and $R^2$, taken together with the carbon atom to which they are attached, form a cycloalkyl ring containing 3-5 carbon atoms;

X is selected from the group consisting of C=O, N—H, $CH_2$, —O—, C=S and —S—;

Y is selected from the group C=O, N—H, $CH_2$, —O—, C=S and —S—; or

X and Y, taken together, represent an olefin linkage wherein X and Y each have a hydrogen atom attached thereto in a cis or trans configuration; and n is 1-7.

Useful dermorphin analogs falling within the scope of formula I include, but are not limited to:

(A) H-Tyrosine-D-Norvaline-Phenylalanine-Ornithine-$NH_2$;

(B) H-Tyrosine-D-Norleucine-Phenylalanine-Ornithine-$NH_2$;

(C) H-Tyrosine-D-Arginine-Phenylalanine-α,γ-diaminobutyric acid-NH$_2$;
(D) H-Tyrosine-D-Arginine-Phenylalanine-Lysine-NH$_2$;
(E) H-Lysine-Tyrosine-D-Arginine-Phenylalanine-Lysine-NH$_2$; and
(F) N$^α$-amidino-Tyrosine-D-arginine-Phenylalanine-Methyl-β-alanine-OH.

In a preferred embodiment, the peptide of the invention is H-Tyrosine-D-Arginine-Phenylalanine-Lysine-NH$_2$ ("DALDA").

In another embodiment, the peptide for use with the invention may be a dermorphin analog of formula II, or a prodrug thereof:

H-Tyrosine-A-Phenylalanine-B—NH$_2$ wherein:

A is selected from the group consisting of D-α-amino acids;

B is selected from the group consisting of α-amino acids; and the overall net positive charge of the peptide is +2 or greater D-α-amino acids useful in forming the compositions of the invention include, but are not limited to, D-norvaline, D-norleucine, D-arginine, D-alanine, D-valine, D-isoleucine, D-leucine, D-serine, D-phenylalanine and D-α,γ-diaminobutyric acid. Alpha-amino acids useful in forming the compositions of the invention include, but are not limited to phenylalanine, para-fluoro phenylalanine, ornithine, α,γ-diaminobutyric acid, lysine, norvaline, arginine, α,β-diaminopropionic acid and homolysine. In a preferred embodiment, the overall net positive charge of the peptide may be +2 or +3.

In a further embodiment, the peptide may be a DALDA derivative of formula III:

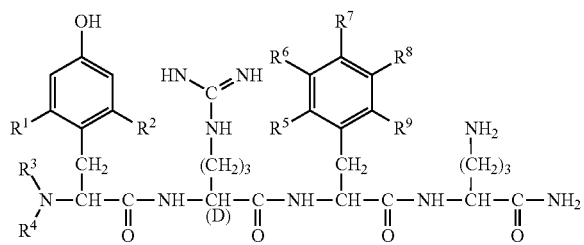

wherein
R$^1$ is selected from
(i) linear or branched C$_1$-C$_6$ alkyl;
(ii) C$_1$-C$_6$ alkoxy,
R$^2$ is selected from
(i) hydrogen;
(ii) linear or branched C$_1$-C$_6$ alkyl;
(iii) C$_1$-C$_6$ alkoxy;
R$^3$ and R$^4$ is each and independently selected from
(i) hydrogen;
(ii) linear or branched C$_1$-C$_6$ alkyl;

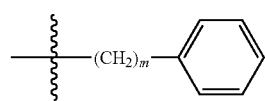

wherein m=1-3;

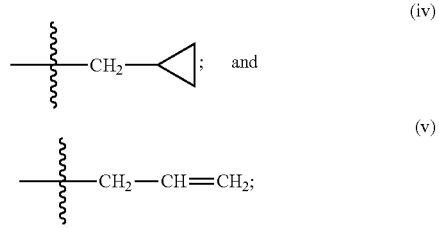

R$^5$, R$^6$, R$^7$, R$^8$ and R9 is each independently selected from
(i) hydrogen;
(ii) halogen, where "halogen" encompasses chloro, fluoro, bromo and iodo; and
(iii) linear or branched C$_1$-C$_6$ alkyl; and
n is an integer of from 1 to 5.

More particularly, in one embodiment of the above-described peptide,
R$^1$ is a linear C$_1$-C$_6$ alkyl;
R$^2$ is a linear C$_1$-C$_6$ alkyl or hydrogen;
R$^3$ and R$^4$ is each and independently selected from a straight C$_1$-C$_6$ alkyl or hydrogen;
R$^5$, R$^6$, R$^7$, R$^8$ and R$^9$ is each and independently selected from
(i) hydrogen;
(ii) a halogen selected from chloro, fluoro, bromo and iodo; and
(iii) linear or branched C$_1$-C$_6$ alkyl, and
n is an integer from 1 to 5.

In an alternate version of the subject embodiment,
R$^1$ is CH$_3$;
R$^2$ is hydrogen or CH$_3$;
R$^3$ and R$^4$ are both hydrogen;
R$^5$, R$^6$, R$^7$, R$^8$ and R$^9$ are all hydrogen; and
n=4.

In a preferred embodiment, the dermorphin analog is a peptide represented by the formula:

H-2,6-dimethyltyrosine-D-Arginine-Phenylalanine-Lysine-NH$_2$. ("DMT-DALDA")

In an additional embodiment of the invention, the peptide is a dermorphin analog of formula IV:

Tyrosine-D-alanine-Xaa-Glycine-Tyrosine-Proline-Serine-NH$_2$ wherein Xaa is L- or D-dimethylphenylalanine.

In a further embodiment of the invention, the peptide for use with the invention is a deltorphin analog of formula V:

Tyrosine-D-alanine-Xaa-Glutamic Acid-Valine-Valine-Glycine-NH$_2$ wherein Xaa is L or D-dimethylphenylalanine.

An alternate embodiment of the invention involves the inclusion of compounds having analgesic and/or cardiovascular activity which, although not peptides, display characteristics which are similar thereto and which are subject to many of the same considerations with regard to transport and adsorption as the peptides described herein. These compounds are agonists or partial agonists of the vanilloid receptor VR1. Examples of these compounds include, but are not limited to:
(i) N-[2-(3,4-dimethylbenzyl)-3-(pivaloyloxy)propyl]-N'-[4-(methylsulfonylamino)benzyl]thiourea; and
(ii) N-(4-tert-butylbenzyl)-N'-[3-methoxy-4-(methylsulfonylamino)benzyl]thiourea.

In an additional embodiment of the invention, the peptide is an enkephalin peptide, or a prodrug thereof. Examples of such enkephalin peptides include, but are not limited to:

(i) H-Tyrosine-Glycine-Glycine-Phenylalanine-Methionine-OH;

(ii) H-Tyrosine-Glycine-Glycine-Phenylalanine-Leucine-OH;

(iii) H-Tyrosine-D-alanine-Glycine-N-methyl-phenylalanine-Glycine-ol; and (iv) analogs thereof.

In still another embodiment, the peptide may be linked to a DMT-Tic-Pharmacaphore having the structure

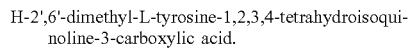

H-2',6'-dimethyl-L-tyrosine-1,2,3,4-tetrahydroisoquinoline-3-carboxylic acid.

Peptides for use in the invention include, but are not limited to those selected from the group consisting of (i) H-DMT-Tic-Glycine-NH-Benzyl; and (ii) H-DMT-Tic-NH—CH(CH$_2$—COOH)-1-H-benzimidazole-2-yl.

The peptides having analgesic and/or cardiovascular activity for use in the invention may be prepared in accordance with Examples 2 and 3 of U.S. Pat. No. 5,602,100 to Brown et al., which is incorporated herein by reference. Example 2 of the subject patent teaches the method of peptide synthesis. Peptides containing c-terminal free acids can be synthesized by linking BOC amino acids using a chloro methyl resin [Merrifield resin], 1% cross linked, 100-200 mesh obtained from Peptides International [Lousiville, Ky.]. Example 3 describes methodology for use in purifying the resultant peptides. In particular, a preferred peptide for use in the invention, i.e., Dmt-DALDA, may be prepared as shown in Example 1 of U.S. Pat. No. 6,703,483 to Schiller, which is also incorporated by reference.

Compounds having analgesic and/or cardiovascular activity which are useful in the invention further include agonists or partial agonists of vanilloid receptor VR1. Methods for preparing these compounds are set forth in, for example, International Patent Publications WO 02/16318 and WO 02/16319 of Suh, et al., both dated Feb. 28, 2002. Both of these publications are incorporated herein by reference.

The pH-Lowering Agent

The total amount of the pH-lowering agent to be administered with each administration of the pharmaceutical composition should preferably be an amount which, when it is released into the intestine, is sufficient to lower the local intestinal pH substantially below the pH optima for proteases found there. The quantity required will necessarily vary with several factors including the type of pH-lowering agent used (discussed below) and the equivalents of protons provided by a given pH-lowering agent. In practice, the amount required to provide good bioavailability is an amount which, when added to a solution of 10 milliliters of 0.1 M sodium bicarbonate, lowers the pH of that sodium bicarbonate solution to no higher than 5.5, and preferably no higher than 4.7, most preferably no higher than 3.5. Enough acid to lower pH, in the foregoing test, to about 2.8 may been used in some embodiments. Preferably at least 300 milligrams, and more preferably at least 400 milligrams of the pH-lowering agent are used in the pharmaceutical composition of the invention. The foregoing preferences relate to the total combined weight of all pH-lowering agents where two or more of such agents are used in combination. The oral formulation should not include an amount of any base which, when released together with the pH-lowering compound, would prevent the pH of the above-described sodium bicarbonate test from dropping to 5.5 or below.

The pH-lowering agent of the invention may be any pharmaceutically acceptable compound that is not toxic in the gastrointestinal tract and is capable of either delivering hydrogen ions (a traditional acid) or of inducing higher hydrogen ion content from the local environment. It may also be any combination of such compounds. It is preferred that at least one pH-lowering agent used in the invention have a pKa no higher than 4.2, and preferably no higher than 3.0. It is also preferred that the pH lowering agent have a solubility in water of at least 30 grams per 100 milliliters of water at room temperature.

Examples of compounds that induce higher hydrogen ion content include aluminum chloride and zinc chloride. Pharmaceutically acceptable traditional acids include, but are not limited to acid salts of amino acids (e.g. amino acid hydrochlorides) or derivatives thereof. Examples of these are acid salts of acetylglutamic acid, alanine, arginine, asparagine, aspartic acid, betaine, carnitine, carnosine, citrulline, creatine, glutamic acid, glycine, histidine, hydroxylysine, hydroxyproline, hypotaurine, isoleucine, leucine, lysine, methylhistidine, norleucine, ornithine, phenylalanine, proline, sarcosine, serine, taurine, threonine, tryptophan, tyrosine and valine.

Other examples of useful pH-lowering compounds include carboxylic acids such as acetylsalicylic, acetic, ascorbic, citric, fumaric, glucuronic, glutaric, glyceric, glycocolic, glyoxylic, isocitric, isovaleric, lactic, maleic, oxaloacetic, oxalosuccinic, propionic, pyruvic, succinic, tartaric, valeric, and the like.

Other useful pH-lowering agents that might not usually be called "acids" in the art, but which may nonetheless be useful in accordance with the invention are phosphate esters (e.g., fructose 1,6 diphosphate, glucose 1,6 diphosphate, phosphoglyceric acid, and diphosphoglyceric acid). CARBOPOL.®. (Trademark BF Goodrich) and polymers such as polycarbophil may also be used to lower pH.

Any combination of pH lowering agent that achieves the required pH level of no higher than 5.5 in the sodium bicarbonate test discussed above may be used. One preferred embodiment utilizes, as at least one of the pH-lowering agents of the pharmaceutical composition, an acid selected from the group consisting of citric acid, tartaric acid and an acid salt of an amino acid.

When DMT-DALDA is the peptide active agent, certain ratios of pH-lowering agent to DMT-DALDA have proven especially effective. It is preferred that the weight ratio of pH-lowering agent to DMT-DALDA exceed 40:1, preferably 400:1 and most preferably 4000:1.

The Absorption Enhancer

The absorption enhancers are preferably present in a quantity that constitutes from 0.1 to 20.0 percent by weight, relative to the overall weight of the pharmaceutical composition (exclusive of the enteric coating). Preferred absorption enhancers are surface active agents which act both as solubility enhancers and uptake enhancers. Generically speaking, "solubility enhancers" improve the ability of the components of the invention to be solubilized in either the aqueous environment into which they are originally released or into the lipophilic environment of the mucous layer lining the intestinal walls, or both. "Transport (uptake) enhancers" (which are frequently the same surface active agents used as solubility enhancers) are those which facilitate the ease by which peptide agents cross the intestinal wall.

One or more absorption enhancers may perform one function only (e.g., solubility), or one or more absorption enhancers may perform the other function only (e.g., uptake), within the scope of the invention. It is also possible to have a mixture of several compounds some of which provide improved solubility, some of which provide improved uptake and/or some of which perform both. Without intending to be bound by theory, it is believed that uptake enhancers may act by (1) increasing disorder of the hydrophobic region of the membrane exterior of intestinal cells, allowing for increased transcellular transport; or (2) leaching membrane proteins resulting in increased transcellular transport; or (3) widening pore radius between cells for increased paracellular transport. Surface active agents are believed to be useful both as solubility enhancers and as uptake enhancers. For example, detergents are useful in (1) solubilizing all of the active components quickly into the aqueous environment where they are originally released, (2) enhancing lipophilicity of the components of the invention, especially the peptide active agent, aiding its passage into and through the intestinal mucus, (3) enhancing the ability of the normally polar peptide active agent to cross the epithelial barrier of the brush border membrane; and (4) increasing transcellular or paracellular transport as described above.

When surface active agents are used as the absorption enhancers, it is preferred that they be free flowing powders for facilitating the mixing and loading of capsules during the manufacturing process. Because of inherent characteristics of certain peptides (e.g., their isoelectric point, molecular weight, amino acid composition, etc.) certain surface active agents interact best with certain peptides. Indeed, some can undesirably interact with the charged portions of certain peptides and thus prevent their absorption, thus undesirably resulting in decreased bioavailability. It is preferred, when trying to increase the bioavailability of peptides that any surface active agent used as an absorption enhancer be selected from the group consisting of (i) anionic surface active agents that are cholesterol derivatives (e.g., bile acids), (ii) cationic surface agents (e.g., acyl carnitines, phospholipids and the like), (iii) non-ionic surface active agents, and (iv) mixtures of anionic surface active agents (especially those having linear hydrocarbon regions) together with negative charge neutralizers. Negative charge neutralizers include but are not limited to acyl carnitines, cetyl pyridinium chloride, and the like. Acyl carnitines (e.g., lauroyl carnitine) are particularly good absorption enhancers. It is also preferred that the absorption enhancer be soluble at acid pH, particularly in the 3.0 to 5.0 range.

To reduce the likelihood of side effects, preferred detergents, when used as the absorption enhancers of the invention, are either biodegradable or reabsorbable (e.g. biologically recyclable compounds such as bile acids, phospholipids, and/or acyl carnitines), preferably biodegradable. Acylcarnitines are believed particularly useful in enhancing paracellular transport.

Absorption enhancers may also include: (a) salicylates such as sodium salicylate, 3-methoxysalicylate, 5-methoxysalicylate and homovanilate; (b) bile acids such as taurocholic, tauorodeoxycholic, deoxycholic, cholic, glycholic, lithocholate, chenodeoxycholic, ursodeoxycholic, ursocholic, dehydrocholic, fusidic, etc.; (c) non-ionic surfactants such as polyoxyethylene ethers (e.g. Brij 36T, Brij 52, Brij 56, Brij 76, Brij 96, Texaphor A6, Texaphor A14, Texaphor A60 etc.), p-t-octyl phenol polyoxyethylenes (Triton X-45, Triton X-100, Triton X-114, Triton X-305 etc.) nonylphenoxypoloxyethylenes (e.g. Igepal CO series), polyoxyethylene sorbitan esters (e.g. Tween-20, Tween-80 etc.); (d) anionic surfactants such as dioctyl sodium sulfosuccinate; (e) lyso-phospholipids such as lysolecithin and lysophosphatidylethanolamine; (f) acylcarnitines, acylcholines and acyl amino acids such as lauroylcarnitine, myristoylcarnitine, palmitoylcarnitine, lauroylcholine, myristoylcholine, palmitoylcholine, hexadecyllysine, N-acylphenylalanine, N-acylglycine etc.; g) water soluble phospholipids such as diheptanoylphosphatidylcholine, dioctylphosphatidylcholine etc.; (h) medium-chain glycerides which are mixtures of mono-, di- and triglycerides containing medium-chain-length fatty acids (caprylic, capric and lauric acids); (i) ethylene-diaminetetraacetic acid; (j) cationic surfactants such as cetylpyridinium chloride; (k) fatty acid derivatives of polyethylene glycol such as Labrasol, Labrafac, etc.; and (l) alkylsaccharides such as lauryl maltoside, lauroyl sucrose, myristoyl sucrose, palmitoyl sucrose, etc.

In some preferred embodiments, and without intending to be bound by theory, cationic ion exchange agents (e.g. detergents) are included to provide solubility enhancement by another possible mechanism. In particular, they may prevent the binding of the peptide active agents to mucus. Preferred cationic ion exchange agents include protamine chloride or any other polycation.

Other Optional Ingredients

It is preferred that a water-soluble barrier separate the pH-lowering agent from the acid resistant protective vehicle. A conventional pharmaceutical capsule may, for example, be used for the purpose of providing this barrier. Many water soluble barriers are known in the art and include, but are not limited to, hydroxypropyl methylcellulose and conventional pharmaceutical gelatins.

In some preferred embodiments, another peptide (such as albumin, casein, soy protein, other animal or vegetable proteins and the like) is included to reduce non-specific adsorption (e.g., binding of peptide to the intestinal mucus barrier) thereby lowering the necessary concentration of the expensive peptide active agent. When added, the peptide is preferably from 1.0 to 10.0 percent by weight relative to the weight of the overall pharmaceutical composition (excluding protective vehicle). Preferably, this second peptide is not physiologically active and is most preferably a food peptide such as soy bean peptide or the like. Without intending to be bound by theory, this second peptide may also increase bioavailability by acting as a protease scavenger that desirably competes with the peptide active agent for protease interaction. The second peptide may also aid the active compound's passage through the liver.

All pharmaceutical compositions of the invention may optionally also include common pharmaceutical diluents, glycants, lubricants, gelatin capsules, preservatives, colorants and the like in their usual known sizes and amounts.

The Protective Vehicle

Any carrier or vehicle that protects the peptide active agent from stomach proteases and then dissolves so that the other ingredients of the invention may be released in the intestine is suitable. Many such enteric coatings are known in the art, and are useful in accordance with the invention. Examples include cellulose acetate phthalate, hydroxypropyl methylethylcellulose succinate, hydroxypropyl methylcellulose phthalate, carboxyl methylethylcellulose and methacrylic acid-methyl methacrylate copolymer. In some embodiments, the active peptide, absorption enhancers such as solubility and/or uptake enhancer(s), and pH-lowering compound(s), are included in a sufficiently viscous protective syrup to permit protected passage of the components of the invention through the stomach.

Suitable enteric coatings for protecting the peptide agent from stomach proteases may be applied, for example, to capsules after the remaining components of the invention have been loaded within the capsule. In other embodiments, enteric coating is coated on the outside of a tablet or coated on the outer surface of particles of active components which are then pressed into tablet form, or loaded into a capsule, which is itself preferably coated with an enteric coating.

It is very desirable that all components of the invention be released from the carrier or vehicle, and solubilized in the intestinal environment as simultaneously as possible. It is preferred that the vehicle or carrier release the active components in the small intestine where uptake enhancers that increase transcellular or paracellular transport are less likely to cause undesirable side effects than if the same uptake enhancers were later released in the colon. It is emphasized, however, that the present invention is believed effective in the colon as well as in the small intestine. Numerous vehicles or carriers, in addition to the ones discussed above, are known in the art. It is desirable (especially in optimizing how simultaneously the components of the invention are released) to keep the amount of enteric coating low. Preferably, the enteric coating adds no more than 30% to the weight of the remainder of pharmaceutical composition (the "remainder" being the pharmaceutical composition exclusive of enteric coating itself). More preferably, it adds less than 20%, especially from 12% to 20% to the weight of the uncoated composition. The enteric coating preferably should be sufficient to prevent breakdown of the pharmaceutical composition of the invention in 0.1N HCl for at least two hours, then capable of permitting complete release of all contents of the pharmaceutical composition within thirty minutes after pH is increased to 6.3 in a dissolution bath in which said composition is rotating at 100 revolutions per minute.

Other Preferences

It is preferred that the weight ratio of pH-lowering agent(s) to absorption enhancer(s) be between 3:1 and 20:1, preferably 4:1-12:1, and most preferably 5:1-10:1. The total weight of all pH-lowering agents and the total weight of all absorption enhancers in a given pharmaceutical composition is included in the foregoing preferred ratios. For example, if a pharmaceutical composition includes two pH-lowering agents and three absorption enhancers, the foregoing ratios will be computed on the total combined weight of both pH-lowering agents and the total combined weight of all three absorption enhancers.

It is preferred that the pH-lowering agent, the peptide active agent and the absorption enhancer (whether single compounds or a plurality of compounds in each category) be uniformly dispersed in the pharmaceutical composition. In one embodiment, the pharmaceutical composition comprises granules that include a pharmaceutical binder having the peptide active agent, the pH-lowering agent and the absorption enhancer uniformly dispersed within said binder. Preferred granules may also consist of an acid core, surrounded by a uniform layer of organic acid, a layer of enhancer and a layer of peptide that is surrounded by an outer layer of organic acid. Granules may be prepared from an aqueous mixture consisting of pharmaceutical binders such as polyvinyl pyrrolidone or hydroxypropyl methylcellulose, together with the pH-lowering agents, absorption enhancers and peptide active agents of the invention.

Manufacturing Process

A preferred pharmaceutical composition of the invention includes a size OO gelatin or HPMC (hydroxypropylmethyl cellulose) capsule filled with 0.25 mg of the active peptide component with analgesic and/or cardiovascular activity, 400 mg of granular citric acid (available for example from Archer Daniels Midland Corp.) and 50 mg lauroyl carnitine (SIGMA)

All of the ingredients are preferably for eventual insertion into the gelatin or HPMC capsule, and are preferably powders which may be added to a blender in any order. Thereafter, the blender is run for about five minutes until the powders are thoroughly intermixed. Then the mixed powders are loaded into the large end of the gelatine capsules. The other end of the capsule is then added, and the capsule snapped shut. 500 or more such capsules may be added to a coating device (e.g., Vector LDCS 20/30 Laboratory Development Coating System (available from Vector Corp., Marion, Iowa)). An enteric coating solution is made as follows. Weigh 500 grams of EUDRAGIT L30. D-55 (a methacrylic acid copolymer with methacylic acid methyl ester, an enteric coating available from ROHM Pharma Polymers Inc., Maidan, Mass.). Add 411 grams distilled water, 15 grams triethyl citrate and 38 grams talc. This amount of coating will be sufficient to coat about 500 size OO capsules.

The capsules are weighed and placed into the drum of the coating machine. The machine is turned on to rotate the drum (now containing capsules) at 24-28 rpm. The temperature of inlet sprayer is preferably about 45.degree. C. Exhaust temperatures are preferably about 30.degree. C. Uncoated capsule temperature is preferably about 25.degree. C. Air flow is about 38 cubic feet per minute.

A tube from the machine is then inserted into the coating solution prepared as discussed above. The pump is then turned on for feeding solution into the coating device. Coating then proceeds automatically. The machine can be stopped at any time to weigh capsules to determine if the coating amount is sufficient. Usually coating is allowed to proceed for 60 minutes. The pump is then turned off for about five minutes while the machine is still running to help dry the coated capsules. The machine can then be turned off. The capsule coating is then complete, although it is recommended that the capsules be air dried for about two days.

Because of the enhanced bioavailability provided by the present invention, the concentration of the expensive active peptide component in the pharmaceutical preparation of the invention may be kept relatively low. Specific formulation examples incorporating the DMT-DALDA peptide are set forth infra.

Treatment of Patients

It is preferred that a single capsule be used at each administration because a single capsule best provides simultaneous release of the polypeptide, pH-lowering agent and absorption enhancers. This is highly desirable because the acid is best able to reduce undesirable proteolytic attack on the polypeptide when the acid is released in close time proximity to release of the polypeptide. Near simultaneous release is best achieved by administering all components of the invention as a single pill or capsule. However, the invention also includes, for example, dividing the required amount of acid and enhancers among two or more capsules which may be administered together such that they together provide the necessary amount of all ingredients. "Pharmaceutical composition," as used herein includes a complete dosage appropriate to a particular administration to a human patient regardless of how it is subdivided so long as it is for substantially simultaneous administration.

For certain indications, it may be preferred to administer a first oral pharmaceutical composition in a capsule or tablet which does not contain a protective acid stable vehicle, such that the components will be relatively rapidly released in the stomach and thus be available for immediate pain relief, i.e., within about 10-20 minutes. Subsequently, additional capsules or tablets formulated according to the invention with a protective vehicle may then be administered, resulting in bioavailability in the intestine of the active ingredient after the longer time interval that is required for gastric emptying, i.e., typically around two hours.

In one embodiment of the invention, a sufficient amount of the peptide (or agonist or partial agonist of vanilloid receptor VR1) is included in the oral formulation of the invention to achieve a serum level (i.e, $C_{max}$) of the peptide (or agonist or partial agonist) of from 200 pg/ml to 20 ng/ml, and, more preferably, from 200 pg/ml to 2 ng/ml. Dosage levels of the active peptide (and/or the agonist or partial agonist) for achieving the above serum levels preferably range from 100 µg to 10 mg and more preferably, from 100 µg to 1 mg. With respect to all of the dosages recommended herein, however, the attending clinician should monitor individual patient response and adjust the dosage accordingly. Moreover, except where otherwise stated, the preferred dosage of the active compounds of the invention is identical for both therapeutic and prophylactic purposes. The dosage for each active component discussed herein is the same, regardless of the disease being treated (or prevented). Furthermore, except where otherwise indicated, the terms "compound" and "composition", and any associated molecular structure may include any possible stereoisomers thereof, in the form of a racemic mixture or in optically active form.

Except where otherwise noted, or where apparent from context, dosages herein refer to weight of active compounds unaffected by pharmaceutical excipients, diluents, carriers or other ingredients, although such additional ingredients are desirably included.

Experimental Results

The following examples are provided only for the purpose of illustration and are not to be construed as limiting the invention in any manner.

Applicants have surprisingly discovered, through the use of in vivo tests involving, respectively, rats and dogs, that administering Dmt-DALDA in the oral formulation described herein provides unexpected improvements in bioavailability of the subject peptide.

With regard to the first series of tests, i.e., on rats, the improved effect is demonstrated by comparing the curves for Formulated DALDA vs. Unformulated DALDA in FIG. 1. In the experiments represented in the subject Figure, six anesthetized rats (which were color-coded as: red, white, blue, orange, green and yellow) were given 0.7 mL Dmt-DALDA (1.6 mg/mL) with a syringe through a 27 gauge needle into the duodenum. This injection procedure was followed due to the technical difficulty inherent in preparing capsules which can be swallowed by small animals the size of a rat. The intraduodanal injection, therefore, mimics the release of the components of an enteric-coated capsule formulation which would pass through the esophagus and stomach and release its contents in the duodenum. Three of the rats (red, white and blue) were given Unformulated Dmt-DALDA in which there were no additional components (i.e., other than the Dmt-DALDA), while the other three rats (orange, green and yellow) were given Formulated Dmt-DALDA which included, in addition to the Dmt-DALDA, 0.5M citric acid and lauroyl carnitine (10 mg/ml). Samples of blood were taken from the carotid artery through an indwelling catheter before and 5, 15, 30, 60 and 120 minutes after the administration of the respective formulations (i.e., Formulated and Unformulated). The blood samples were centrifuged and the resulting plasma supernatants were stored frozen at −20° C. The plasma samples were subsequently analyzed for Dmt-DALDA by high-performance liquid chromatography (HPLC) through a 50×4.6 mm polysulfoethyl-aspartamide column with a mobile phase of 15.4 mM potassium phosphate (pH 3), 210 mM sodium chloride, and 25% acrylonitrile at a flow rate of 1.5 mL/min. Peptide was detected with an ultraviolet (UV) detector set at a wavelength of 210 nm. The results show that Dmt-DALDA was virtually undetectable in rats given unformulated Dmt-DALDA, whereas as much as 8 µg/mL of Dmt-DALDA was detected in rats given Dmt-DALDA formulated in citric acid and lauroyl carnitine. These results clearly demonstrate that formulating Dmt-DALDA in an oral formulation according to the present invention increases the $C_{max}$ 19-fold and the AUC 110-fold compared to the unformulated peptide (see Table II below). Table I (below) sets forth the values upon which the curves in FIG. 1 are based. Table I, moreover, provides the standard deviations for the data obtained regarding each of the test rats, which standard deviations are also indicated in FIG. 1.

TABLE I

| | unformulated | | | | | |
|---|---|---|---|---|---|---|
| min | red µg/mL | white µg/mL | blue µg/mL | avg | sdev | sem |
| 0 | 0.00 | 0.00 | 0.00 | 0.00 | 0.00 | 0.00 |
| 5 | 1.54 | 0.00 | 0.00 | 0.51 | 0.89 | 0.51 |
| 15 | 0.00 | 0.00 | 0.00 | 0.00 | 0.00 | 0.00 |
| 30 | 0.00 | 0.00 | 0.00 | 0.00 | 0.00 | 0.00 |
| 60 | 0.00 | 0.00 | 0.00 | 0.00 | 0.00 | 0.00 |
| 120 | 0.00 | 0.00 | 0.00 | 0.00 | 0.00 | 0.00 |

| | formulated | | | | | |
|---|---|---|---|---|---|---|
| min | orange | green | yellow | avg | sdev | sem |
| 0 | 0.00 | 0.00 | 0.00 | 0.00 | 0.00 | 0.00 |
| 5 | 14.15 | 2.74 | 7.19 | 8.03 | 5.75 | 3.32 |
| 15 | 0.80* | 4.19 | 10.75 | 7.47 | 4.64 | 3.28 |
| 30 | 12.02 | 3.21 | 10.37 | 8.53 | 4.69 | 2.71 |
| 60 | died | 2.40 | 7.10 | 4.75 | 3.32 | 2.35 |
| 120 | | 0.00 | 2.29 | 1.14 | 1.62 | 1.14 |

*poor sampling, not included in mean

Table II (below) summarizes the pharmacokinetic parameters in rats of orally administered unformulated and formulated Dmt-DALDA as those terms are defined above. Data for the individual rats shown in FIG. 1 are summarized. $C_{max}$ refers to the maximum concentration of peptide detected in the rat plasma. The area under the curve (AUC) is a measure of the extent of peptide absorption and is calculated by the trapezoidal rule from a plot of peptide concentration as a function of time. $T_{max}$ indicates when the maximum concentration of the Dmt-DALDA in the blood serum was obtained.

TABLE II

| | Unformulated | | | |
|---|---|---|---|---|
| Rat | Red DALDA | White DALDA | Blue DALDA | Avg (n = 3) DALDA |
| Cmax (µg/mL) | 1.54 | 0.00 | 0.00 | 0.51 |
| AUC (µg/mL-min) | 11.52 | 0.00 | 0.00 | 3.84 |
| Tmax (min) | 5.00 | | | 5.00 |

| | Formulated | | | |
|---|---|---|---|---|
| Rat | Orange DALDA | Green DALDA | Yellow DALDA | Avg (N = 3) DALDA |
| Cmax (µg/mL) | 14.15 | 4.19 | 10.75 | 9.69 |
| AUC (µg/mL-min) | 206.28 | 253.16 | 809.91 | 423.12 |
| Tmax (min) | 5.00 | 15.00 | 15.00 | 11.67 |

As shown in Table II, the $C_{max}$ and AUC for Dmt-DALDA was significantly enhanced when the peptide was administered in a "formulated" solution containing citric acid (pH-lowering agent) and lauroyl carnitine (absorption enhancer).

A second series of tests was carried out, as noted above, using beagle dogs. The improved bioavailability of orally administered Dmt-DALDA is demonstrated in this second series of tests by comparing the curves for (1) non-enteric coated salmon calcitonin (sCT) and (2) non-enteric coated Dmt-DALDA (DALDA) in FIG. 2A with the curves for (3) enteric coated sCT and (4) enteric coated DALDA in FIG. 2B. In the experiments represented in FIGS. 2A and 2B, size 00 HPLC capsules were each filled with 758 mg of a powdered blend consisting of citric acid (643 mg), lauroyl carnitine (66 mg), talc (33 mg), salmon calcitonin (sCT) (13 mg) and Dmt-DALDA (2.4 mg). Half of the capsules were coated with an enteric coating solution of L30D-55, while the remaining 50% of the capsules were not coated. Four fasted dogs were each given 1 uncoated capsule, and 2 weeks later they were each given an enteric coated capsule. After administration of each capsule, samples of blood were taken at 15 minute intervals from an indwelling catheter for up to 4 hours. The blood samples were centrifuged and the resulting plasma supernatants were stored frozen at −20° C. The plasma samples were subsequently analyzed for sCT by a direct ELISA, and for Dmt-DALDA by HPLC-mass spectrometry performed as set forth in Wan, H. and Desiderio, D., *Quantitation of [DMT¹] DALDA in ovine plasma by on-line liquid chromatography/quadrapole time-of-flight mass spectrometry, Rapid Communications in Mass Spectrometry*, 2003; 17, 538-546, the contents of which are incorporated herein by reference.

Figures 2A, 2B:
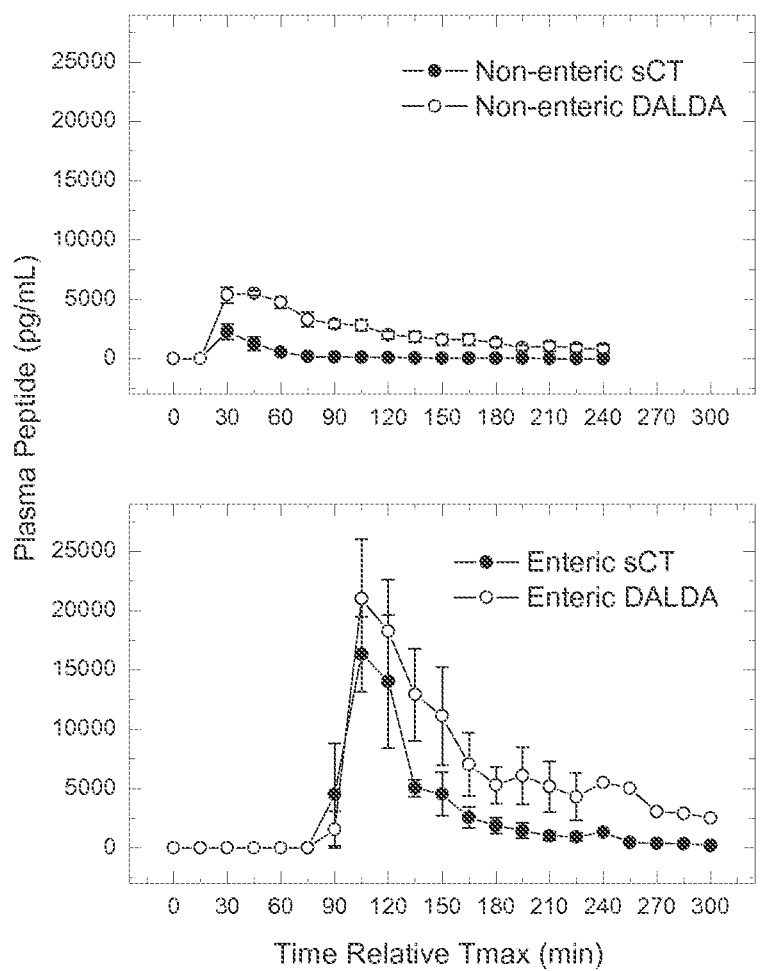
FIG. 2A and FIG. 2B provide, in graphical form, pharmacokinetic profiles following administration to beagle dogs of salmon calcitonin (sCT) plus Dmt-DALDA with citric acid and lauroyl carnitine, in a solid dosage capsule formulation, either without (FIG. 2A) or with (FIG. 2B) an enteric coating.

The results summarized in FIGS. 2A and 2B as plasma peptide concentration normalized to a 1 mg dose as a function of time relative to the average $T_{max}$, (i.e., the time at which the maximum amount of peptide was detected) indicate that both peptides, i.e., sCT and Dmt-DALDA, were detected in dogs given uncoated or enteric coated capsules. However, nearly three times as much Dmt-DALDA as sCT was detected in dogs given uncoated capsules; whereas, nearly equal amounts of both peptides were detected in dogs given enteric coated capsules. Moreover, nearly four times as much Dmt-DALDA was detected in the plasma of dogs given enteric coated capsules than those given non-coated capsules. Furthermore, nearly eight times as much sCT was detected in the plasma of dogs given enteric coated capsules than non-coated capsules. The maximum concentration of Dmt-DALDA and sCT in dogs given uncoated capsules was seen 30 minutes after their administration, whereas the maximum concentration of these materials when given in coated capsules was seen 105 minutes after their administration, thus providing the additional time necessary for the oral formulation to pass through the stomach while remaining protected from the proteolytic enzymes therein. These results clearly demonstrate that coating the capsules with an enteric polymer such that the capsule does not release its contents until reaching the small intestine significantly enhances peptide absorption. Table III (below) sets forth the values upon which the curves in FIGS. 2A and 2B are based. The results are summarized in the tables as plasma peptide concentration normalized to a 1 mg dose as a function of time. Table II, moreover, provides the standard deviations for the data obtained regarding each of the test dogs, which standard deviations are also indicated in FIGS. 2A and 2B.

TABLE III

| | Dog 1 | | Dog 2 | | Day 3 | | Day 4 | |
|---|---|---|---|---|---|---|---|---|
| Min | sCT pg/mL | DALDA pg/mL | sCT pg/mL | DALDA pg/mL | sCT pg/mL | DALDA pg/mL | sCT pg/mL | DALDA pg/mL |
| Non-enteric Coated Capsules Containing Citric Acid and Lauroyl Carnitine | | | | | | | | |
| 0 | 0 | 0 | 0 | 0 | 0 | 0 | 0 | 0 |
| 15 | 0 | 0 | 0 | 0 | 0 | 0 | 0 | 0 |
| 30 | 2648 | 4108 | 3148 | 6473 | 0 | 0 | 971 | 5456 |
| 45 | 1343 | 5104 | 2151 | 5602 | | | 278 | 5788 |
| 60 | 561 | 4066 | 897 | 5726 | | | 163 | 4481 |
| 75 | 273 | 2407 | 229 | 4523 | | | 101 | 2934 |
| 90 | 140 | 2780 | 182 | 3568 | | | 69 | 2382 |
| 105 | 121 | 1938 | 122 | 3444 | | | 45 | 3054 |
| 120 | 89 | 1627 | 69 | 2614 | | | 26 | 1759 |
| 135 | 51 | 1158 | 44 | 2697 | | | 16 | 1627 |
| 150 | 31 | 830 | 39 | 2407 | | | 12 | 1544 |
| 165 | 23 | 913 | 22 | 2531 | | | 0 | 1324 |
| 180 | 16 | 705 | 15 | 2075 | | | 0 | 1191 |
| 195 | 11 | 581 | 0 | 1328 | | | 0 | 851 |
| 210 | 0 | 544 | 0 | 1867 | | | 0 | 722 |
| 225 | 0 | 436 | 0 | 1535 | | | 0 | 672 |
| 240 | 0 | 402 | 0 | 1494 | | | 0 | 556 |

TABLE III-continued

| | Dog 1 | | Dog 2 | | Day 3 | | Day 4 | |
|---|---|---|---|---|---|---|---|---|
| Min | sCT pg/mL | DALDA pg/mL | sCT pg/mL | DALDA pg/mL | sCT pg/mL | DALDA pg/mL | sCT pg/mL | DALDA pg/mL |
| Enteric Coated Capsules Containing Citric Acid and Lauroyl Carnitine | | | | | | | | |
| 0 | 0 | 0 | 0 | 0 | 0 | 0 | 0 | 0 |
| 15 | 0 | 0 | 0 | 0 | 0 | 0 | 0 | 0 |
| 30 | 407 | 0 | 0 | 0 | 0 | 0 | 0 | 0 |
| 45 | 22650 | 29440 | 0 | 0 | 0 | 0 | 0 | 0 |
| 60 | 25136 | 25224 | 0 | 0 | 0 | 0 | 0 | 0 |
| 75 | 6444 | 19768 | 0 | 0 | 0 | 0 | 0 | 0 |
| 90 | 8167 | 19021 | 0 | 0 | 0 | 0 | 0 | 0 |
| 105 | 4344 | 12324 | 0 | 0 | 0 | 0 | 13111 | 4577 |
| 120 | 3193 | 8108 | 0 | 0 | 0 | 0 | 13147 | 12116 |
| 135 | 2710 | 10714 | 0 | 0 | 13219 | 21494 | 6841 | 10207 |
| 150 | 1706 | 9349 | 0 | 0 | 10151 | 19378 | 4251 | 6307 |
| 165 | 1283 | 6743 | 0 | 0 | 4410 | 12697 | 2448 | 5158 |
| 180 | 1301 | 5502 | 0 | 0 | 2983 | 9100 | 1468 | 3884 |
| 195 | 459 | 5008 | 0 | 0 | 1825 | 4876 | 1192 | 2896 |
| 210 | 347 | 3021 | 0 | 0 | 1194 | 4772 | 867 | 2664 |
| 225 | 331 | 2896 | 0 | 0 | 734 | 4884 | 686 | 2490 |
| 240 | 179 | 2527 | 0 | 0 | 626 | 3651 | 515 | 1851 |

Table IV (below) summarizes the pharmacokinetic parameters in dogs of orally administered sCT and Dmt-DALDA when administered in non-enteric coated versus enteric coated capsules. Peptide was not detected from 1 dog in each group due to (a) Dog 3 vomiting the uncoated capsule and (b) delayed gastric emptying in Dog 2 provided with an enteric coated capsule. $C_{max}$ and AUC are as defined with regard to Table II above.

The improvement in oral bioavailability achieved with the Dmt-DALDA peptide in accordance with the present invention, i.e., H-2,6-dimethyltyrosine-D-Arginine-Phenylalanine-Lysine-NH$_2$, is believed to adequately support an expectation of similarly improved results with the remaining active agents described herein. With no intention to be bound by theory, applicants submit in explanation therefor that DALDA and other analgesic peptides that are analogs of

TABLE IV

| | Dog | | | | | | | | | |
|---|---|---|---|---|---|---|---|---|---|---|
| | Dog 1 | | Dog 2 | | Dog 3 | | Dog 4 | | Avg (n = 3) | |
| | sCT | dmt-DALDA | sCT | dmt-DALDA | sCT | dmt-DALDA | sCT | dmt-DALDA | sCT | dmt-DALDA |
| Non-Enteric Capsule | | | | | | | | | | |
| Cmax (pg/mL) | 2648 | 5104 | 3148 | 6473 | 0 | 0 | 971 | 5788 | 2256 | 5788 |
| AUC (pg/mL-min) | 79620 | 410944 | 103772 | 707054 | 0 | 0 | 25227 | 510934 | 69539 | 542977 |
| Tmax (min) | 30 | 45 | 30 | 30 | | | 30 | 45 | 30 | 40 |
| Enteric Capsule | | | | | | | | | | |
| Cmax (pg/mL) | 25136 | 29440 | 0 | 0 | 13219 | 21494 | 13147 | 12116 | 17167 | 21017 |
| AUC (pg/mL-min) | 1178504 | 2375695 | 0 | 0 | 522432 | 1185373 | 664016 | 768361 | 788317 | 1443143 |
| Tmax (min) | 60 | 45 | | | 135 | 135 | 120 | 120 | 105 | 100 |

As shown in Table IV, the $C_{max}$ and AUC values for both sCT and Dmt-DALDA were significantly enhanced when the peptides were administered in enteric coated capsules versus in non enteric-coated capsules. The $C_{max}$ of enteric coated Dmt-DALDA is 4-fold higher than that of non enteric coated Dmt-DALDA. Surprisingly, the bioavailability of both enteric coated and non-coated Dmt-DALDA is better than that of sCT. It would be expected that the bioavailability of a molecule such as Dmt-DALDA, which is positively charged and hydrophilic, would be extremely poor. The data indicates that when this peptide is administered in combination with the ingredients of the present invention, either with or without an enteric coating, however, the bioavailability is unexpectedly increased to the point where it is superior to that of sCT, a molecule that has previously been shown to be highly bioavailable when formulated according to the present invention.

dermorphin or deltorphin, as well as other opioid peptides, are highly charged molecules. For example, Dmt-DALDA has a 3+ net charge. It would be expected that these net positive charges would cause the peptide to bind to the negatively charged mucous layer that lines the gastrointestinal tract, thus reducing the bioavailability of the peptide. It is believed, although applicants are not to be bound by such belief, that the negatively charged citric acid (i.e., the pH-lowering agent), which is in excess in the formulation, would neutralize some or all of the positive charges on the peptide and thus prevent the interaction between the peptide and the mucous layer. Additionally, applicants believe that the positive charge on the acylcarnitine absorption enhancer neutralize the negative charge on the mucous layer in the immediate vicinity of the release of the capsule or tablet contents, and therefore would further prevent the positively charged peptide from binding with the mucous layer. The peptide thus remains available to traverse the epithelial layer in the gastrointestinal tract by paracellular transport through the tight junctions between cells, which are relaxed due to the presence of the acylcarnitine. One of ordinary skill in this art would therefore reasonably expect that the additional active compounds described herein, e.g., the various peptides and their prodrugs, which have a similar size, charge and hydrophilicity to Dmt-DALDA, would themselves achieve an unexpectedly improved degree of bioavailability when administered in the oral formulation taught and claimed herein.

Although the present invention has been described in relation to particular embodiments thereof, many other variations and modifications and other uses will become apparent to those skilled in the art. The present invention therefore is not limited by the specific disclosure herein, but only by the claims.

What is claimed is:

1. A single solid dosage capsule comprising:
   a peptide comprising a 2,6-dimethyltyrosine (Dmt) residue or a prodrug thereof;
   at least one pharmaceutically acceptable pH-lowering agent having a pKa no higher than 4.2 and comprising a carboxylic acid, wherein the at least one pH-lowering agent is one of acetylsalicylic acid, ascorbic acid, citric acid, fumaric acid, glucuronic acid, glyceric acid, glycocholic acid, glyoxylic acid, isocitric acid, lactic acid, maleic acid, oxaloacetic acid, oxalosuccinic acid, pyruvic acid, succinic acid, tartaric acid, or combinations thereof, wherein the weight ratio of the at least one pH lowering agent to the peptide exceeds 40:1; and
   at least one absorption enhancer.

2. The solid dosage capsule of claim 1 wherein the peptide further comprises an arginine residue, a phenylalanine residue, and a lysine residue.

3. The solid dosage capsule of claim 1 wherein the pH-lowering agent is citric acid.

4. The solid dosage capsule of claim 1 wherein the at least one absorption enhancer comprises an acylcarnitine.

5. The solid dosage capsule of claim 4 wherein the acylcarnitine is lauroyl carnitine.

6. The solid dosage capsule of claim 1 further comprising an enteric coating.

7. The solid dosage capsule of claim 6 wherein the enteric coating is present at a weight which is no more than 20% of the weight of the remainder of the solid dosage capsule excluding the enteric coating.

8. The solid dosage capsule of claim 6 further comprising a water-soluble barrier separating the at least one pH-lowering agent from the enteric coating.

9. The solid dosage capsule of claim 1 wherein the at least one pH-lowering agent is present in the single dosage form in a quantity which, if added to 10 milliliters of 0.1M aqueous sodium bicarbonate solution, would be sufficient to lower the pH of the solution to no higher than 3.5.

10. The solid dosage capsule of claim 1 comprising a therapeutically-effective amount of the peptide comprising the 2,6-dimethyltyrosine (Dmt) residue or prodrug thereof to achieve analgesia.

11. A method for relieving pain comprising administering to a subject in need thereof a therapeutically-effective amount of the solid dosage capsule of claim 1.

12. A single solid dosage capsule comprising:
    a deltorphin analog or a prodrug thereof comprising a dimethylphenylalanine residue;
    at least one pharmaceutically acceptable pH-lowering agent having a pKa no higher than 4.2 and comprising a carboxylic acid, wherein the at least one pH-lowering agent is one of acetylsalicylic acid, ascorbic acid, citric acid, fumaric acid, glucuronic acid, glyceric acid, glycocholic acid, glyoxylic acid, isocitric acid, lactic acid, maleic acid, oxaloacetic acid, oxalosuccinic acid, pyruvic acid, succinic acid, tartaric acid, or combinations thereof, wherein the weight ratio of the at least one pH lowering agent to the peptide exceeds 40:1; and
    at least one absorption enhancer.

13. The solid dosage capsule of claim 12 wherein the deltorphin analog is Tyrosine-D-alanine-Xaa-Glutamic Acid-Valine-Valine-Glycine-$NH_2$, wherein Xaa is L- or D-dimethylphenylalanine.

14. The solid dosage capsule of claim 12 wherein the pH-lowering agent is citric acid.

15. The solid dosage capsule of claim 12 wherein the at least one absorption enhancer comprises lauroyl carnitine.

16. The solid dosage capsule of claim 12 further comprising an enteric coating.

17. The solid dosage capsule of claim 16 wherein the enteric coating is present at a weight which is no more than 20% of the weight of the remainder of the solid dosage capsule excluding the enteric coating.

18. The solid dosage capsule of claim 12 wherein the pH-lowering agent is present in the single dosage form in a quantity which, if added to 10 milliliters of 0.1M aqueous sodium bicarbonate solution, would be sufficient to lower the pH of the solution to no higher than 3.5.

19. The solid dosage capsule of claim 12 comprising a therapeutically-effective amount of the deltorphin analog or prodrug thereof comprising the dimethylphenylalanine residue to achieve analgesia.

20. A method for relieving pain comprising administering to a subject in need thereof a therapeutically-effective amount of the solid dosage capsule of claim 12.

21. The solid dosage capsule of claim 1 wherein the at least one pH-lowering agent is present in the single dosage form in a quantity which, if added to 10 milliliters of 0.1M aqueous sodium bicarbonate solution, would be sufficient to lower the pH of the solution to no higher than 5.5.

22. The solid dosage capsule of claim 1 wherein the at least one pH-lowering agent is present in the single dosage form in a quantity which, if added to 10 milliliters of 0.1M aqueous sodium bicarbonate solution, would be sufficient to lower the pH of the solution to no higher than 4.7.

23. The solid dosage capsule of claim 1 wherein the weight ratio of the at least one pH lowering agent to the peptide exceeds 400:1.

24. The solid dosage capsule of claim 1 comprising at least 300 mg of the at least one pH-lowering agent.

25. The solid dosage capsule of claim 1 wherein the at least one pH-lowering agent is one of fumaric acid, maleic acid, oxaloacetic acid, oxalosuccinic acid, pyruvic acid, tartaric acid, or combinations thereof and has a pKa no higher than 3.0.

* * * * *

SEQUENCE LISTING

```
<160> NUMBER OF SEQ ID NOS: 13

<210> SEQ ID NO 1
<211> LENGTH: 4
<212> TYPE: PRT
<213> ORGANISM: Artificial
<220> FEATURE:
<223> OTHER INFORMATION: Synthetic construct
<220> FEATURE:
<221> NAME/KEY: PEPTIDE
<222> LOCATION: (2)..(2)
<223> OTHER INFORMATION: Xaa is selected from the group consisting of
      D-alpha-amino acids
<220> FEATURE:
<221> NAME/KEY: PEPTIDE
<222> LOCATION: (4)..(4)
<223> OTHER INFORMATION: Xaa is selected from the group consisting of
      alpha-amino acids

<400> SEQUENCE: 1

Tyr Xaa Phe Xaa
1

<210> SEQ ID NO 2
<211> LENGTH: 7
<212> TYPE: PRT
<213> ORGANISM: Artificial
<220> FEATURE:
<223> OTHER INFORMATION: Synthetic construct
<220> FEATURE:
<221> NAME/KEY: PEPTIDE
<222> LOCATION: (3)..(3)
<223> OTHER INFORMATION: Xaa is L- or D-dimethylphenylaline

<400> SEQUENCE: 2

Tyr Ala Xaa Gly Tyr Pro Ser
1               5

<210> SEQ ID NO 3
<211> LENGTH: 7
<212> TYPE: PRT
<213> ORGANISM: Artificial
<220> FEATURE:
<223> OTHER INFORMATION: Synthetic construct
<220> FEATURE:
<221> NAME/KEY: PEPTIDE
<222> LOCATION: (3)..(3)
<223> OTHER INFORMATION: Xaa is L- or D-dimethylphenylaline

<400> SEQUENCE: 3

Thr Ala Xaa Glu Val Val Gly
1               5

<210> SEQ ID NO 4
<211> LENGTH: 4
<212> TYPE: PRT
<213> ORGANISM: Artificial
<220> FEATURE:
```

```
<223> OTHER INFORMATION: Synthetic construct
<220> FEATURE:
<221> NAME/KEY: PEPTIDE
<222> LOCATION: (2)..(2)
<223> OTHER INFORMATION: Xaa is D-Norvaline
<220> FEATURE:
<221> NAME/KEY: PEPTIDE
<222> LOCATION: (4)..(4)
<223> OTHER INFORMATION: Xaa is ornithine

<400> SEQUENCE: 4

Tyr Xaa Phe Xaa
1

<210> SEQ ID NO 5
<211> LENGTH: 4
<212> TYPE: PRT
<213> ORGANISM: Artificial
<220> FEATURE:
<223> OTHER INFORMATION: Synthetic construct
<220> FEATURE:
<221> NAME/KEY: PEPTIDE
<222> LOCATION: (2)..(2)
<223> OTHER INFORMATION: Xaa is norleucine
<220> FEATURE:
<221> NAME/KEY: PEPTIDE
<222> LOCATION: (4)..(4)
<223> OTHER INFORMATION: Xaa is ornithine

<400> SEQUENCE: 5

Tyr Xaa Phe Xaa
1

<210> SEQ ID NO 6
<211> LENGTH: 4
<212> TYPE: PRT
<213> ORGANISM: Artificial
<220> FEATURE:
<223> OTHER INFORMATION: Synthetic construct
<220> FEATURE:
<221> NAME/KEY: PEPTIDE
<222> LOCATION: (4)..(4)
<223> OTHER INFORMATION: Xaa is alpha,gamma-diaminobutyric acid

<400> SEQUENCE: 6

Tyr Arg Phe Xaa
1

<210> SEQ ID NO 7
<211> LENGTH: 4
<212> TYPE: PRT
<213> ORGANISM: Artificial
<220> FEATURE:
<223> OTHER INFORMATION: Synthetic construct

<400> SEQUENCE: 7

Tyr Arg Phe Lys
1

<210> SEQ ID NO 8
<211> LENGTH: 5
<212> TYPE: PRT
<213> ORGANISM: Artificial
<220> FEATURE:
<223> OTHER INFORMATION: Synthetic construct

<400> SEQUENCE: 8

Lys Tyr Arg Phe Lys
1               5
```

```
<210> SEQ ID NO 9
<211> LENGTH: 4
<212> TYPE: PRT
<213> ORGANISM: Artificial
<220> FEATURE:
<223> OTHER INFORMATION: Synthetic construct

<400> SEQUENCE: 9

Tyr Arg Phe Ala
1

<210> SEQ ID NO 10
<211> LENGTH: 3
<212> TYPE: PRT
<213> ORGANISM: Artificial
<220> FEATURE:
<223> OTHER INFORMATION: Synthetic construct

<400> SEQUENCE: 10

Arg Phe Lys
1

<210> SEQ ID NO 11
<211> LENGTH: 5
<212> TYPE: PRT
<213> ORGANISM: Artificial
<220> FEATURE:
<223> OTHER INFORMATION: Synthetic construct

<400> SEQUENCE: 11

Tyr Gly Gly Phe Met
1               5

<210> SEQ ID NO 12
<211> LENGTH: 5
<212> TYPE: PRT
<213> ORGANISM: Artificial
<220> FEATURE:
<223> OTHER INFORMATION: Synthetic construct

<400> SEQUENCE: 12

Tyr Gly Gly Phe Leu
1               5

<210> SEQ ID NO 13
<211> LENGTH: 5
<212> TYPE: PRT
<213> ORGANISM: Artificial
<220> FEATURE:
<223> OTHER INFORMATION: Synthetic construct

<400> SEQUENCE: 13

Tyr Ala Gly Phe Gly
1               5
```